United States Patent [19]

Weinstein et al.

[11] Patent Number: 5,230,347
[45] Date of Patent: Jul. 27, 1993

[54] APPARATUS AND METHOD FOR MEASURING TACTILE SENSATION LOCALIZED ON THE OPTIC CORNEA

[75] Inventors: Curt Weinstein, Danbury, Conn.; Sidney Weinstein, South Salem, N.Y.; Ronald Drozdenko, Woodbury, Conn.

[73] Assignee: Neurocommunication Research Laboratories, Inc., Danbury, Conn.

[21] Appl. No.: 845,069

[22] Filed: Mar. 3, 1992

[51] Int. Cl.$^5$ .............................................. A61B 19/00
[52] U.S. Cl. .................................... 128/740; 128/648
[58] Field of Search .............. 128/648, 652, 739, 740, 128/774

[56] References Cited

U.S. PATENT DOCUMENTS 3,232,099  2/1966  Motchenbacher .................. 128/648

FOREIGN PATENT DOCUMENTS 0061777  10/1982  European Pat. Off. ............ 128/652
748282   4/1956  United Kingdom ................ 128/652

OTHER PUBLICATIONS

Millodot, M. (1971). Article entitled Corneal Sensitivity and Contact Lenses. *The Optician*, 162, 23-24.

Millodot, M. (1972). Article entitled Diurnal Variation of Corneal Sensitivity. *British Journal of Ophthalmology*, 56, 844-847.

Millodot, M. (1973). Article entitled Objective Measurement of Corneal Sensitivity. *Acta Ophthalmologica*, 51, 325-334.

Zaidman, G., Weinstein, C., Weinstein, S. & Drozdenko, R. (1988). Article entitled A New Corneal Microaesthesiometer. Presented at meetings of The Association for Research in Vision and Ophthalmology.

Beuerman, R. W. & Tanelian, D. L. (1979). Article entitled Corneal Pain Evoked by Thermal Stimulation. *Pain*, 7, 1-14.

Boberg-Ans, J. (1956). Article entitled on the Corneal Sensitivity. *Acta Ophthalmologica*, 34, 149.

Draeger, J. (1984). Article entitled *Corneal Sensitivity*. New York: Springer-Verlag.

Jalavisto, E., Orma,. & Tawast, M. (1951). Article entitled Aging and the Relation Between Stimulus Intensity and Duration in Corneal Sensitivity. *Acta Physiologica Scandanavica*, 23, 224-233.

Martin, X. Y. & Safran, A. B. (1988). Article entitled Corneal Hypesthesia. *Survey of Ophthalmology*, 33, 28-40.

(List continued on next page.)

Primary Examiner—Max Hindenburg
Attorney, Agent, or Firm—Frishauf, Holtz, Goodman & Woodward

[57] ABSTRACT

Apparatus for the determination of corneal thresholds, for example the corneal center, through the use of air flow to specific corneal sites, comprises a "stimulate" air flow path leading from an air compressor through a stimulate nozzle to the cornea for stimulation, and a "non-stimulate" air flow path leading from the air compressor to a calibrate nozzle, so that the force in the stimulate nozzle may be set before stimulation. A further "exhaust" air flow path is provided quickly to exhaust air from the stimulate nozzle to provide a sharp turn-off of the force of the air flow applied to the optic cornea, thereby obtaining a substantially rectangular stimulation characteristic. The nozzle is wide and flat with a dimple or recess formed substantially at or near the center thereof where air exits therefrom, so that the force and extent of air needed to stimulate the cornea is limited. Air flow is provided with a rapid off-flow, allowing for a more rectangular air flow characteristic, for stimulation of the cornea without damage and pain to the cornea. The nozzle may be positioned near to the cornea of a patient to be tested through the use of an eyeglass frame-type mounting and adjustment mechanism, or a headgear-type mounting and adjustment mechanism, or a slit lamp-type adjustment mechanism having a headrest member.

30 Claims, 13 Drawing Sheets

OTHER PUBLICATIONS

Millodot, M. (1968). Article entitled Psychophysical Scaling of Corneal Sensitivity. *Psychonomic Science*, 12, 401–402.

Millodot, M. (1969). Article entitled Studies on the Sensitivity of the Cornea. *Precision Cosmetic Digest*, 9, 1–6.

Millodot, M. (1977b). Article entitled The Influence of Age on the Sensitivity of the Cornea. *Investigative Ophthalmology & Visceral Sci.*, 16, 240–242.

Millodot, M. (1981). Article entitled Corneal Sensitivity. International Ophthamology Clinics *Complications of Contact Lenses*, Summer 21.

Millodot, M. & Lamont. A. (1974). Article entitled Influence of Menstruation on Corneal Sensitivity. *British J. of Ophthalomology*, 58, 752–756.

Millodot, M. & Larson, W. (1967). Article entitled Effect of Bending of the Nylon Thread of the Cochet--Bonnet Corneal Aesthesiometer Upon Recorded Pressure. *The Contact Lens*, 1, 5–7.

Millodot, M. & O'Leary, D. J. (1981). Article entitled Corneal Fragility and Its Relationship to Sensitivity. *Acta Ophthalmologica*, 59, 820–826.

Morganroth, J. & Richman, L. (1969). Article entitled Changes in the Corneal Reflex in Patients Wearing Contact Lenses. *Journal of Pediatric Ophthalmology*, 6, 207.

Millodot, M. (1974). Article entitled Effect of Soft Lenses on Corneal Sensitivity. *Acta Ophthalmologica*, 52, 603–608.

Millodot, M. (1975a). Article entitled Do Blue Eyed People Have More Sensitive Corneas Than Brown Eyed People? *Nature, 1 255, 151–152.*

Millodot, M. (1975b). Article entitled Effect of Hard Contact Lenses on Corneal Sensitivity and Thickness. *Acta Opthalmologica*, 576–584.

Millodot, M. (1976a). Article entitled Corneal Sensitivity in People with the Same and with Different Iris Color. *Investigative Ophthalmology*, 15, 861–862.

Millodot, M. (1976b). Article entitled Effect of the Length of Wear of Contact Lenses on Corneal Sensitivity. *Acta Ophthalmologica*, 54, 721–730.

Millodot, M. (1977a). Article entitled The Influence of Pregnancy on the Sensitivity of the Cornea. *British J. of Ophthalmology*, 61.

APPARATUS AND METHOD FOR MEASURING TACTILE SENSATION LOCALIZED ON THE OPTIC CORNEA

BACKGROUND OF THE INVENTION

This invention relates to the field of corneal esthesiometry. Corneal esthesiometry is concerned with the measuring of thresholds of the optic cornea to pressure stimuli. Specifically, this invention relates to the determination of thresholds for specific loci on the optic cornea. Other regions of the surface of the eye can be evaluated, as well.

This invention is related to previous procedures that have been used to measure corneal sensation. The two current popular methods employed to assess corneal thresholds use a solid probe to stimulate the cornea. A different recent method employs laser light that heats the cornea. Historically, air has been blown at the cornea to elicit reports of sensation or a blink reflex.

Concerning the two current popular methods, for each stimulation, the probe approaches the eye in view of the person being tested. The first popular known device, Millodot's Cochet-Bonnet esthesiometer, is a hand-held or a device-held variant of the von Frey esthesiometer. The Cochet-Bonnet esthesiometer is an esthesiometer which controls the stimulation force by means of varying the length of the probe, a wire. The wire is used to stimulate the cornea. Stimulation with the wire, however, has been shown to damage the cornea, and visible damage seen after testing with the Cochet-Bonnet apparatus is associated with an induced increase in threshold. See, for example, Millodot, M., & O'Leary, J. 1981: Corneal Fragility and Its Relationship to Sensitivity, *Acta Ophthalmologica*, 59, 820–826.

The second popular device, the Draeger corneal esthesiometer, is a more sophisticated mechanical device which thrusts or places a metal pin, the probe, against the cornea. The Draeger device cannot be used for people with normal corneal thresholds without causing pain. See, for example, Martin, X. Y., & Safran, A. B. 1988: Corneal hypoesthesia, *Survey of Ophthalmology*, 33, 28–40. Thus the Draeger device cannot measure thresholds in people with normal sensitivity.

With respect to the use of lasers, the current laser technique uses the tear-film of the eye to transduce laser energy into heat energy, which is then felt by the subject. The perceptual experience of the subject from heat production is nociceptive rather than due to a temperature gradient (i.e., heat or warmth). See, for example, Beuerman, R. W. & Tanelian, D. L. 1979: Corneal pain evoked by thermal stimulation, *Pain*, 7, 1–14.

In addition to these devices, devices made by others have used air to stimulate the cornea. See, for example, Goldberg et al., 1943; Morganroth & Richman, 1943; Jalavisto et al., 1951; and Boberg-Ans, 1956. The esthesiometer made by Jalavisto is representative of air-based (or gas-based) corneal esthesiometers. Jalavisto made an air-based corneal esthesiometer which stimulated the entire corneal surface at once. In these air-based devices, though, other nearby structures (body portions) were inadvertently stimulated (by air diffracting off the blocking edge of the rotating disk). For example, the eye lid, nose, or sclera was probably inadvertently stimulated. When nearby structures are inadvertently stimulated, the tester doesn't know if the resultant threshold is from the cornea or from some other structure. Boberg-Ans dismisses such esthesiometers, stating "It may thus be seen that the air-puff-technique contains so many problems and uncertainties that it cannot be employed for clinical scientific measurement of corneal study" (p. 161).

The entire contents of all of the references listed at the end of this specification are incorporated herein by reference.

SUMMARY OF THE INVENTION

The present invention has as an object to measure thresholds by delivering nonpainful, nondamaging stimulation to all persons, even those with new corneal transplants. The present invention achieves this object by stimulating specific parts of the cornea, without inadvertently stimulating nearby structures and without approaching the cornea with each stimulation.

In order to deliver calibrated stimulation, the present invention comprises a control means and a holder and nozzle means. The control means comprises a compressor from which air flows into a multi-way valve. Two main air flow paths with the same resistance to air are provided. A first path is the stimulation path, which leads from the compressor, preferably then to a rotometer, and then through a nozzle to the cornea. A second non-stimulate air flow path may lead from the compressor, preferably then to the rotometer, and then to a calibrate nozzle.

The advantage of this new procedure in using a second, equally resistive air flow path, is that it allows the air flow to be set prior to stimulation. By internally deflecting the air to and from the person, structures (body parts) nearby the cornea are not inadvertently stimulated. When internally deflecting air from the person, stimulus levels are established.

In order to achieve a more rectangular distribution of stimulation air flow for the present invention, the multi-way valve connects the nozzle adjacent the cornea to an exhaust opening to hasten the turn-off of the stimulus air flow. The multi-way valve thus releases the pressure in the nozzle faster that it would normally be released by leaving the nozzle via only its nozzle opening. By releasing the air pressure in the nozzle faster, the trailing or turn-off edge of the stimulus is more rectangular than it would normally be. The air flow can thus be provided according to a rapid flow-off. In a preferred arrangement, the multi-way valve is a 4-way valve.

In addition, to provide safety for the eye being stimulated, the present invention provides a nozzle having a wide, substantially flat surface towards the eye. The present invention further provides placing an indentation or recess around the orifice of the nozzle, making the force-flow relationship similar to a pointy needle and solving the problems normally associated with placing a flat face about the eflux of the nozzle. The present invention therefore employs a nozzle with a dimple or recess in the flat front face thereof.

The present invention further provides for an eyeglass means and a headgear device for holding and positioning the nozzle safely and accurately near to the cornea of a patient to be tested.

Further objects and advantages of the present invention will become apparent from a consideration of the drawings and ensuing description.

DETAILED DESCRIPTION

The device for measuring tactile sensation localized on the optic cornea according to the present invention will now be described with reference to the Figures. A parts inventory of main components comprising the present invention is listed in Table 1.

Figure 1:
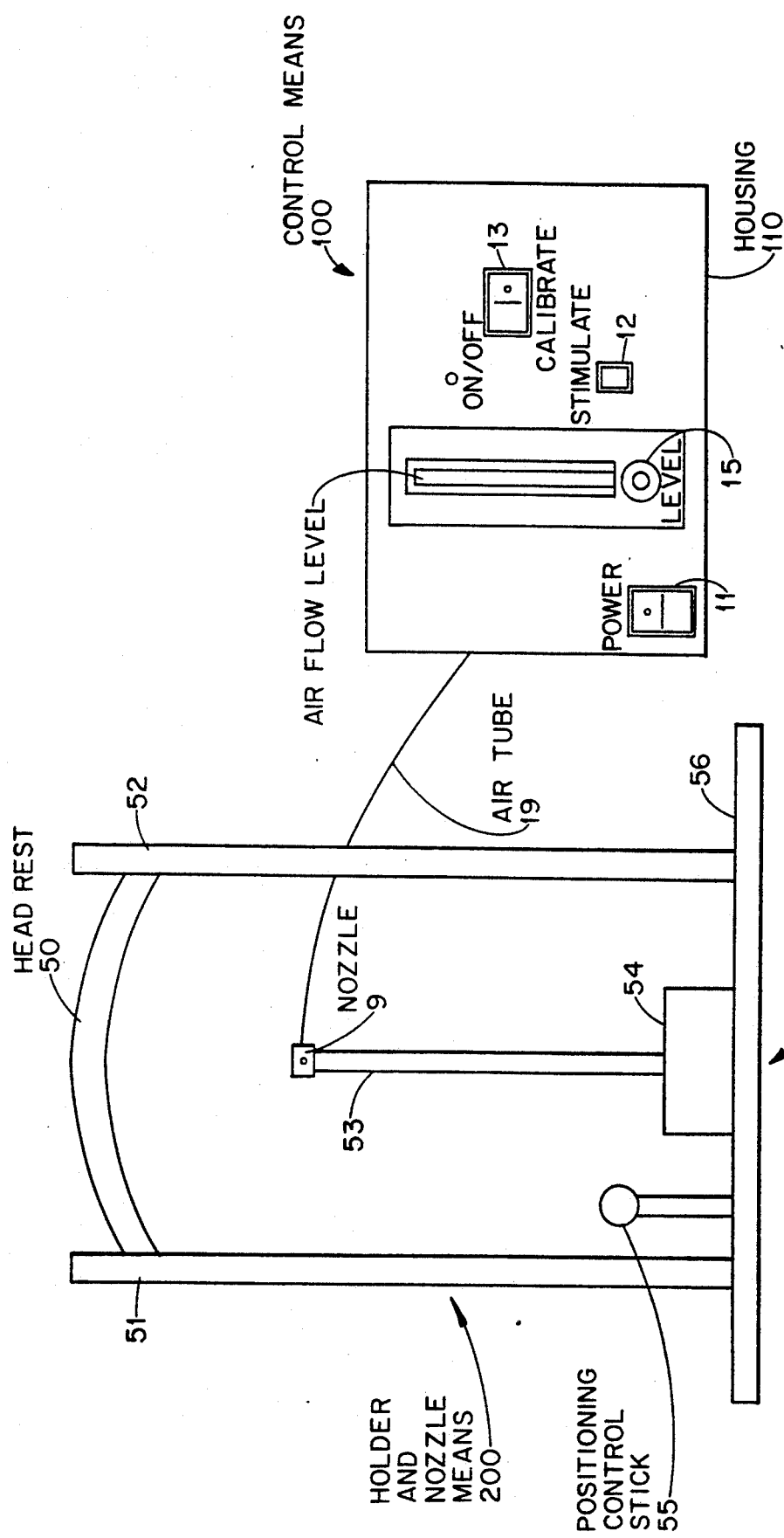
FIG. 1 shows an overall schematic view of a system of the present invention, showing the control means and holder and nozzle means of the present invention.

As shown in FIG. 1, the present invention comprises two main parts, a control means 100, and a holder and nozzle means 200.

Figure 2:
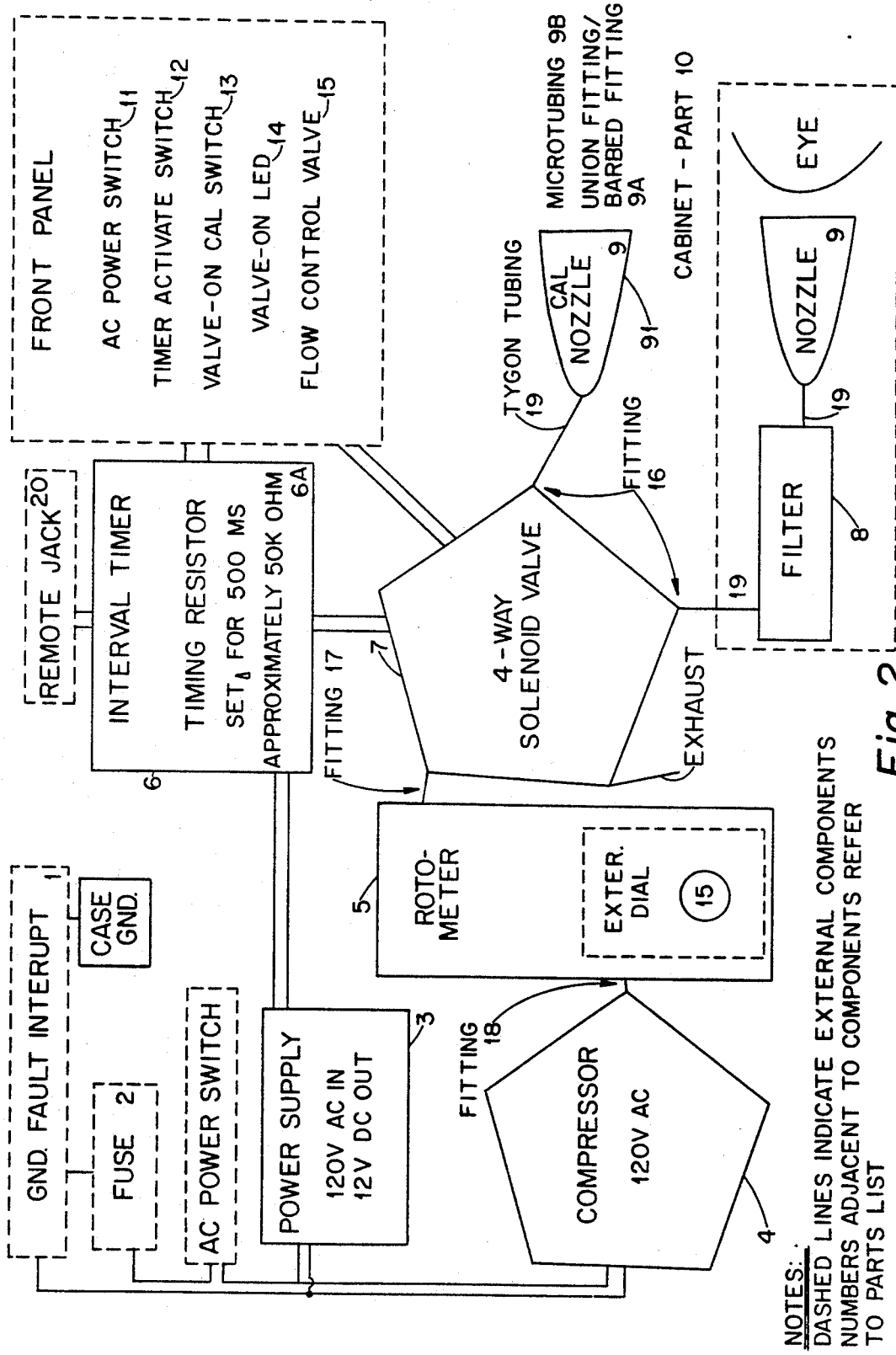
FIG. 2 is a schematic of the stimulation circuit, showing paths of power, air flow and control as well as the nozzle relationship to the eye.
Figure 12:
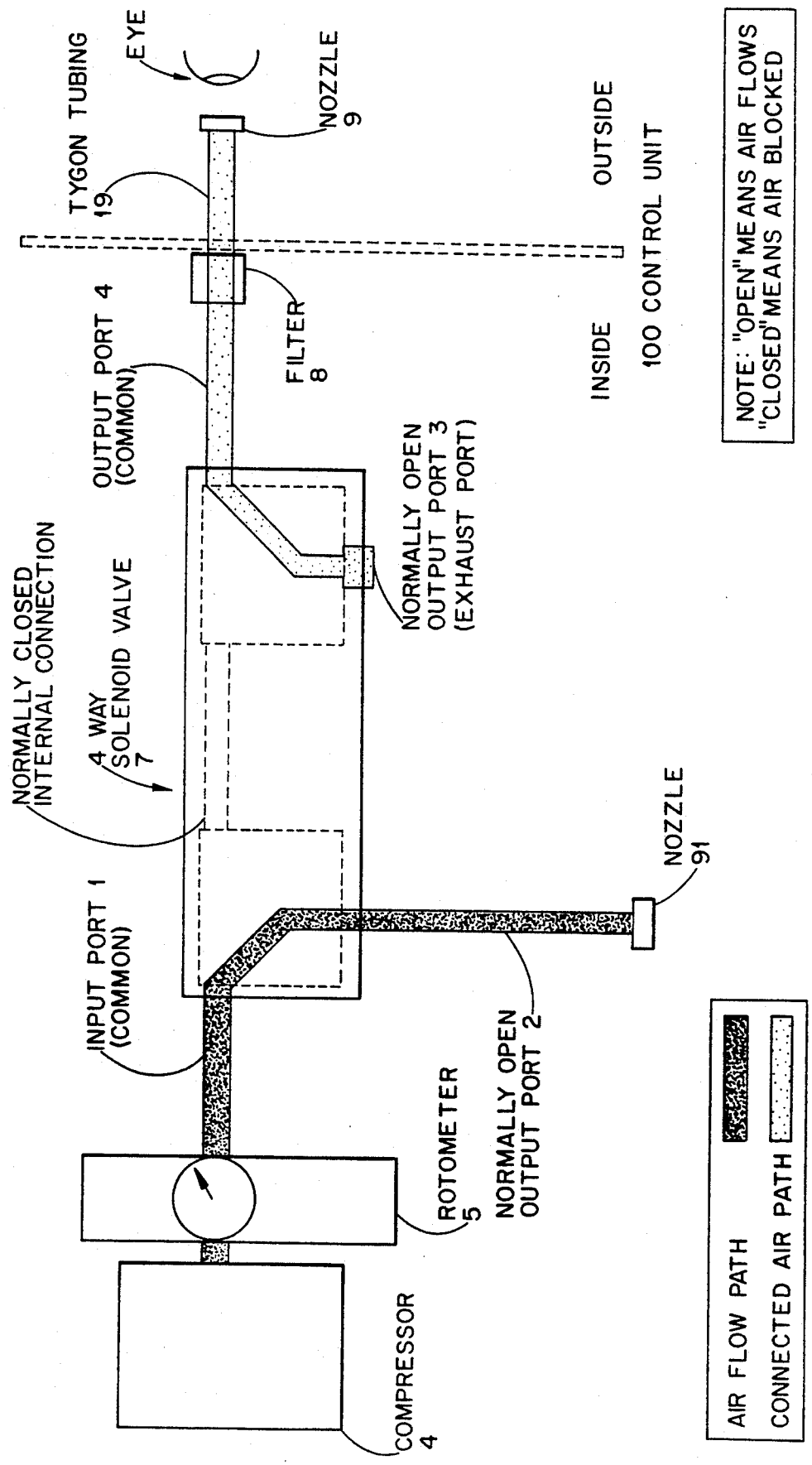
FIG. 12 shows the air path for the "non stimulate" state (air flow path) and the exhaust path (connected air path).

The control means, as shown in FIG. 2, comprises an air compressor 4 which is fixed by sound attenuating construction to a housing 110 (FIG. 1) of the control means 11. The output of the air compressor 4 is connected by loose-fitting (leaky) air connections 18 to a rotometer 5. Rotometer 5 is connected to a 4-way valve 7 (i.e., 4 port valve 7) by means of a fitting or tubing 17, as shown in FIG. 12. The rotometer 5 and the 4-way valve 7 are used to set the force of air stimulation, as seen in FIG. 12. The rotometer 5 connects to port 1 of the 4-way valve 7. Port 1 connects through port 2 to calibrate nozzle 91, as seen in FIG. 12. Calibrate nozzle 91 matches the resistance to air passage of stimulate nozzle 9, thus allowing rotometer 5 to set the stimulation level.

The rotometer 5 in the present invention provides a way to set air flow, as opposed to air pressure, to control the force (pressure) on the stimulated site. Thus as opposed to conventional methods where air pressure is controlled, the problems and uncertainties associated therewith which preclude clinical or scientific measurement of corneal sensitivity are avoided by the present invention. Air pressure is intuitively the correct way to control the air, and, further, allows the user to use a single air path for the device instead of the dual air paths of the present invention (dual air paths: one to stimulate and one to set stimulation level). However, problems result with such air pressure controlled systems. The present invention does not use air pressure to control the stimulation level since its problems are hard to overcome. The present invention uses air flow control (which is not intuitive) instead of air pressure control. Boberg-Ans [1956] stated regarding his attempted air-puff esthesiometer: "It may thus be seen that the air-puff technique contains so many problems and uncertainties that it cannot be employed for clinical or scientific measurement of corneal sensitivity." Boberg-Ans did not seem to notice (as well as experts in the field, e.g., from the National Institutes of Health) that when he attempted to copy Jalivisto's system he changed to a pressure-controlled system, thus making his evaluations irrelevant—he employed air pressure control, not air flow control.

Figure 11:
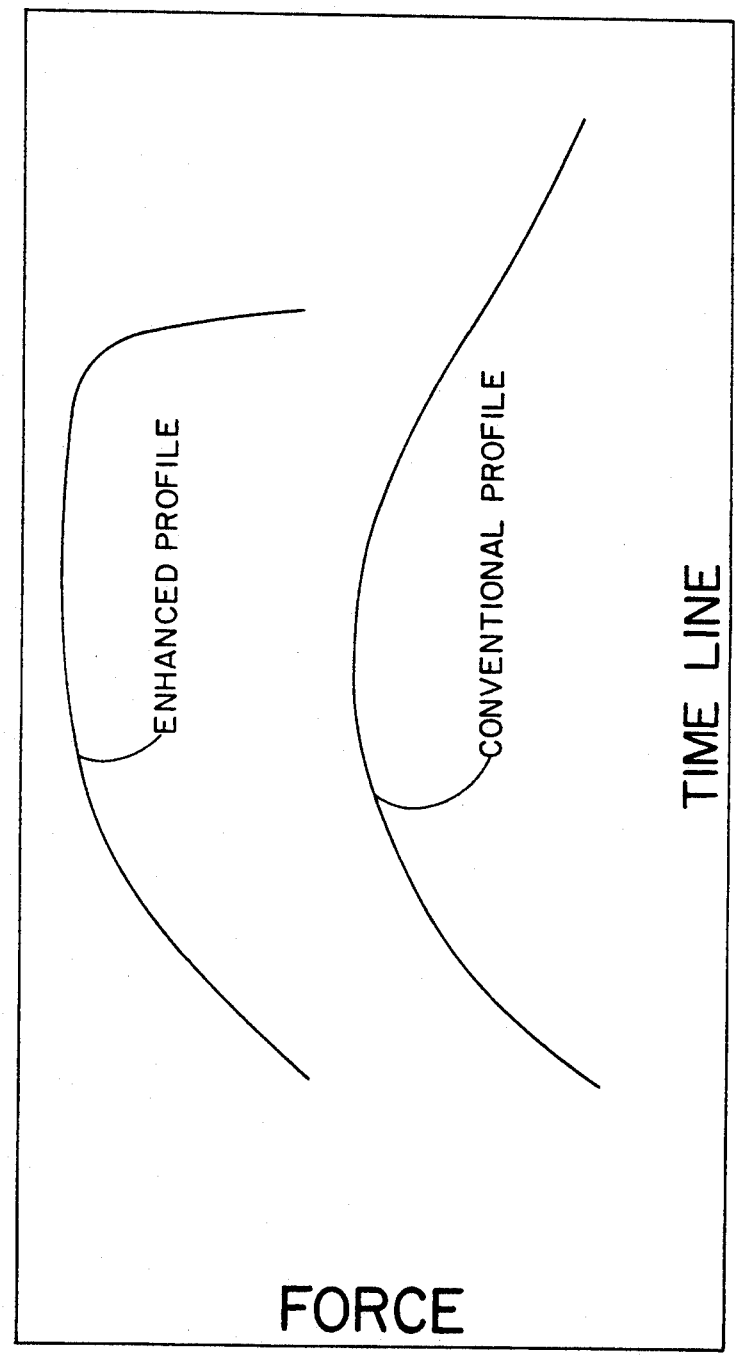
FIG. 11 is a chart showing the enhanced effect of air force as a function of time, showing the enhanced air cut-off effect of the present invention.

The 4-way valve 7 is also used in the present invention to modify the characteristic shape of the profile of the force of stimulation. That is, a rectangular air stimulation pulse is desirable. As shown in FIG. 11, the conventional air pulse looks more rounded. The 4-way valve 7 is used to make the trailing edge of the stimulus more rectangular, as seen in FIG. 11. At the time of termination of the air stimulation pulse, nozzle 9 is connected through port 4 to port 3 of 4-way valve 7 as seen in FIG. 12. Port 3 exhausts excess air away from nozzle 9 to make the trailing edge of the stimulus more rectangular, as seen in FIG. 11.

The rotometer 5 is connected by tight-fitting air connections 17 to port 1 of the 4-way valve 7. The 4-way valve 7 is normally in the "non-stimulate" (NON STIMULATE) position (FIG. 12). In the "NON STIMULATE" air flow path position, air is not delivered to the cornea via the stimulate nozzle 9. In the "STIMULATE" position (FIG. 12A), a "stimulate air flow path" is established so that air is delivered to the cornea via the stimulate nozzle 9. That is, there are two main air flow paths in the present invention, namely: the "non-stimulate air flow path" shown in FIG. 12, and the "stimulate air flow path" shown in FIG. 12A.

Figure 3:
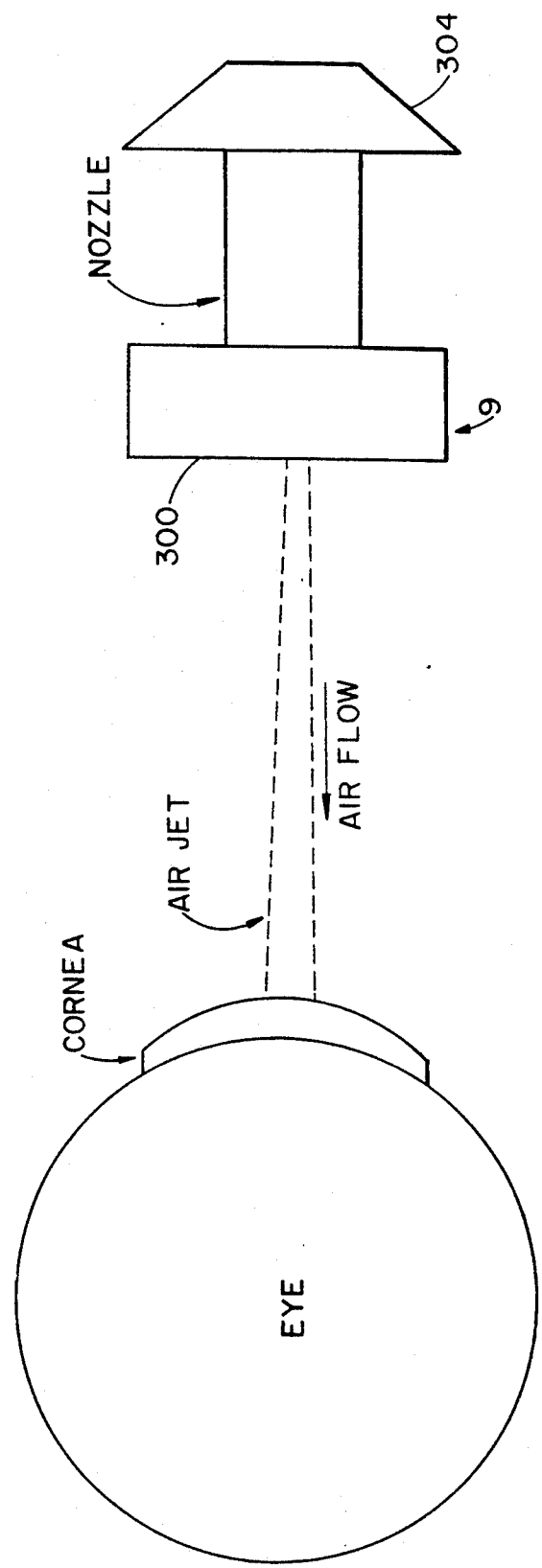
FIG. 3 is a view showing the nozzle in relation to the eye, and showing air flow from the nozzle to the eye.

The stimulate air flow path (FIG. 12A) leads from the rotometer 5 to the cornea. Specifically, the path starts at the air compressor 4, then to the rotometer 5, then through 4-way valve 7, then through a filter 8, then exits the housing 110 via a tube 19, then enters the stimulate nozzle 9, and then exits the outlet of nozzle 9 to stimulate the cornea (see FIGS. 3 and 12A).

The other path (NON-STIMULATE air flow path) leads from the air compressor 4, to the rotometer 5, to port 1 of the 4-way valve 7, to port 2 of the 4-way valve 7, and then to calibrate nozzle 91. The resistances to air flow of the two paths (stimulate and non-stimulate air flow paths) are made to be equal. Except as noted above, all air fittings are without leaks (i.e., air tight). During stimulation, the 4-way valve 7 is actuated to cause air from the rotometer 5 to follow the path (FIG. 12A) through the filter 8, tube 19 and nozzle 9, which leads to the eye. The duration of stimulation is set, for example, to one-half second (500 msec) by means of the timer 6 connected to 4-way valve 7.

When the control means 100 is turned on, the 4-way valve 7 is unactuated and in its "non-stimulate" state (FIG. 12). In this state, the rotometer 5 can be set to deliver the desired stimulus size, because the air traverses through the calibration nozzle 91 which has the same resistance to air flow as the stimulate nozzle 9. Also, during the time when the 4-way valve 7 is unactuated, the stimulate nozzle 9 is connected to the exhaust port of valve 7, as seen in FIG. 12, to create an exhaust air flow path. The exhaust connection is relevant only for a moment after the timed actuation, to cause the stimulation air pulse to more rapidly end. At offset (turning off) of the timer 6, the air pressure near the stimulate nozzle 9 more rapidly equilibrates with room air pressure, because air more rapidly exits through both the large exhaust port and the stimulate nozzle 9 than through only the stimulate nozzle alone. When a stimulate means (i.e., a switch) is pushed, the calibrated stream of air is routed to the stimulate nozzle 9 (see FIG. 12A) for 0.5 seconds (timing controlled by timer 6).

Figure 12A:
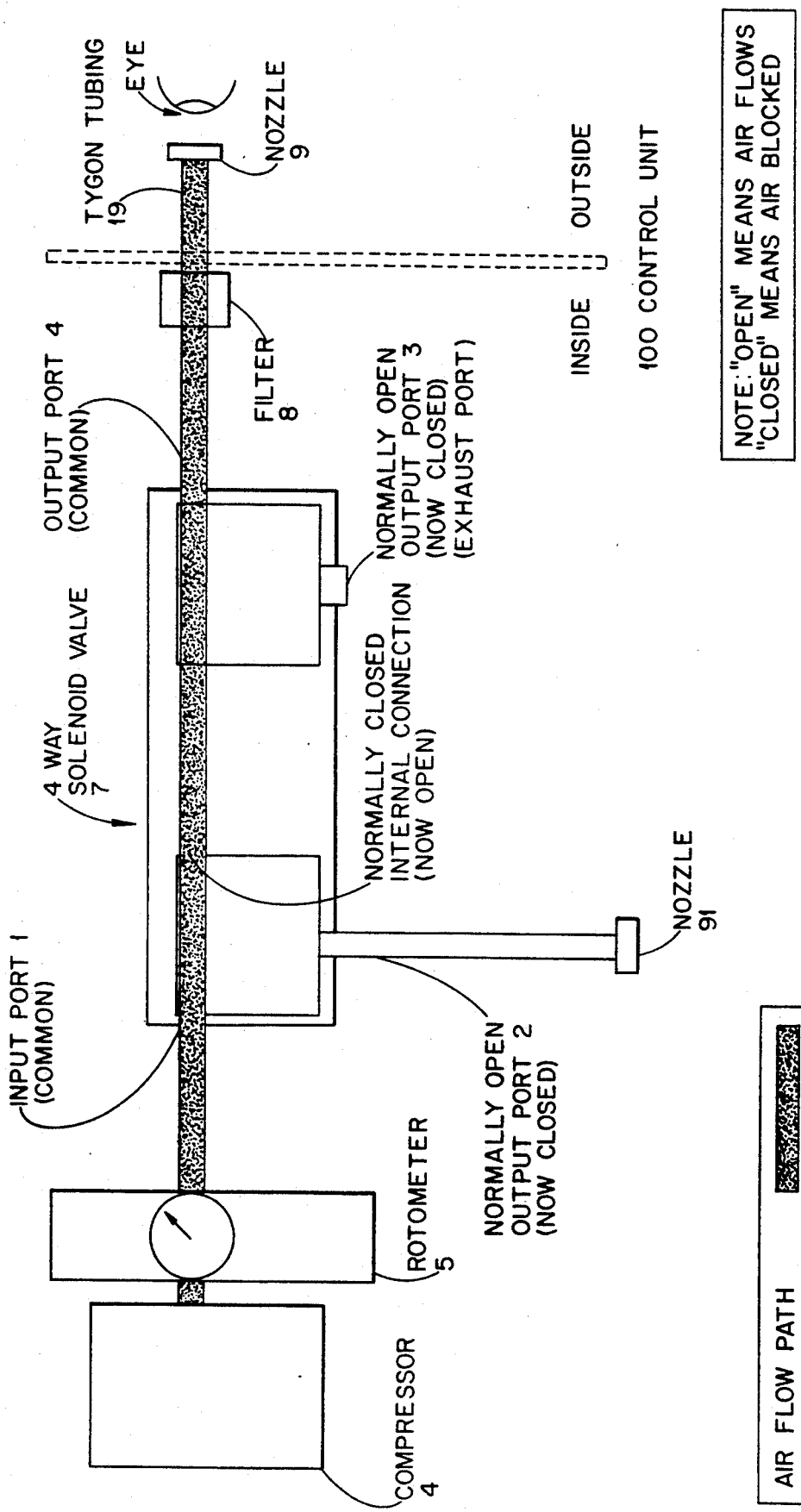
FIG. 12A shows the air path for the "stimulate" state.

Stimulation ceases at the end of the timed duration and the 4-way valve 7 then connects the air in the nozzle 9 to the air in the housing 110 via valve 7 and port 3, the exhaust line (FIG. 12). During stimulation, 4-way valve 7 passes the air to the nozzle 9 via port 4 (FIG. 12A). Air flowing through the nozzle 9 is used to stimulate discrete two-millimeter wide areas (other configurations have stimulated 1.5 mm wide, etc.) on the surface of the optic cornea.

Figure 6:
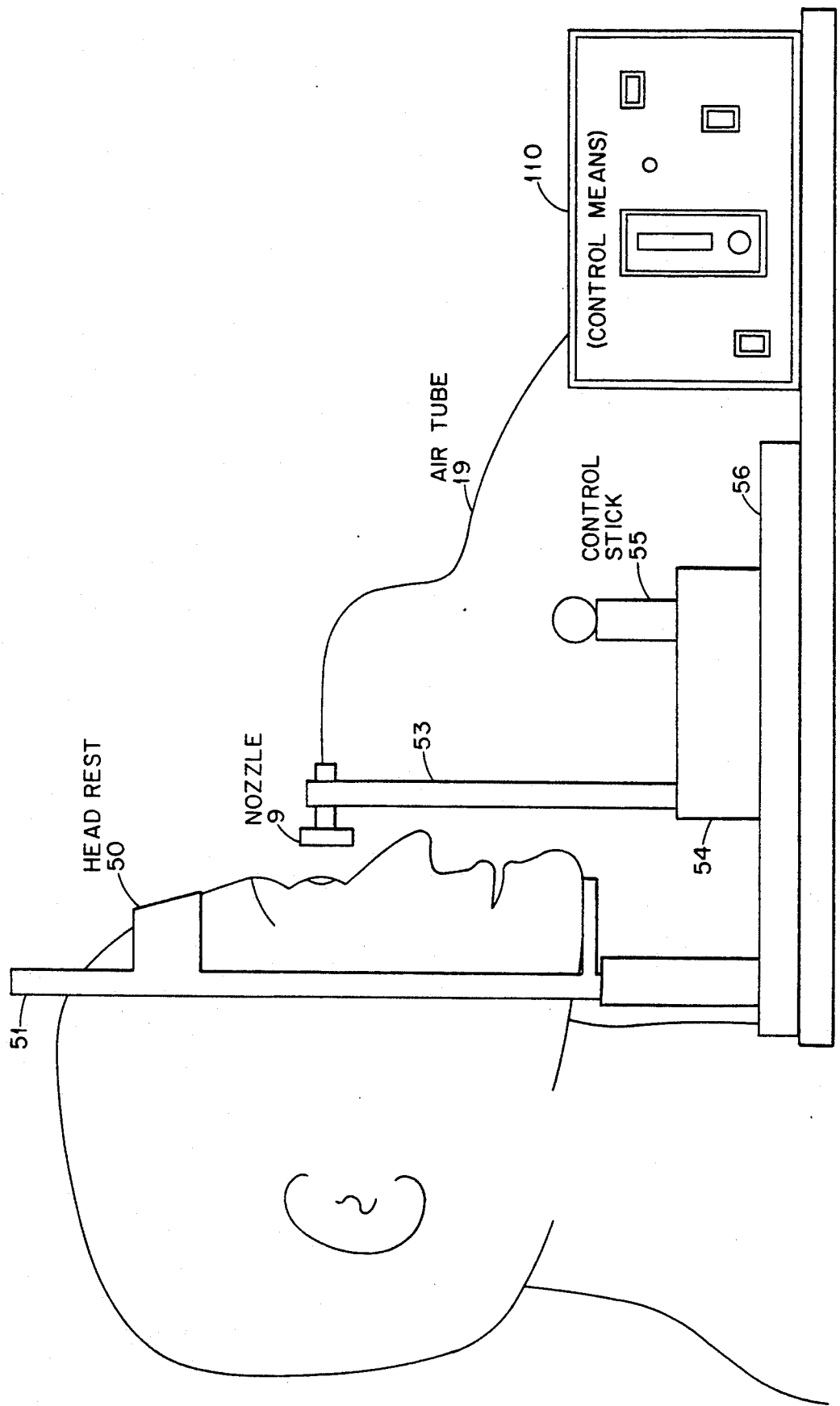
FIG. 6 is a side schematic view of a slit lamp being used to place the nozzle near the cornea of the eye.

The holder and nozzle means 200 is connected to the control means 100 through a flexible air tube 19 (e.g., Tygon tubing, 0.25" ID, 3 feet long). The holder for the nozzle means shown in FIGS. 1 and 6 comprises a head rest member 50 supported by two upright members 51, 52, which is conventional, and against which a head of a patient is placed, as shown in FIG. 6. The nozzle 9 is mounted on an upright support member 53 which is connected to a movable block 54 which is movable under the control of a control stick 55 to position the nozzle 9 adjacent to the cornea of a patient. The entire apparatus is mounted on a base 56. Head rest-type holders of the type shown in FIGS. 1 and 6 are conventional and are not described further herein.

Figure 10:
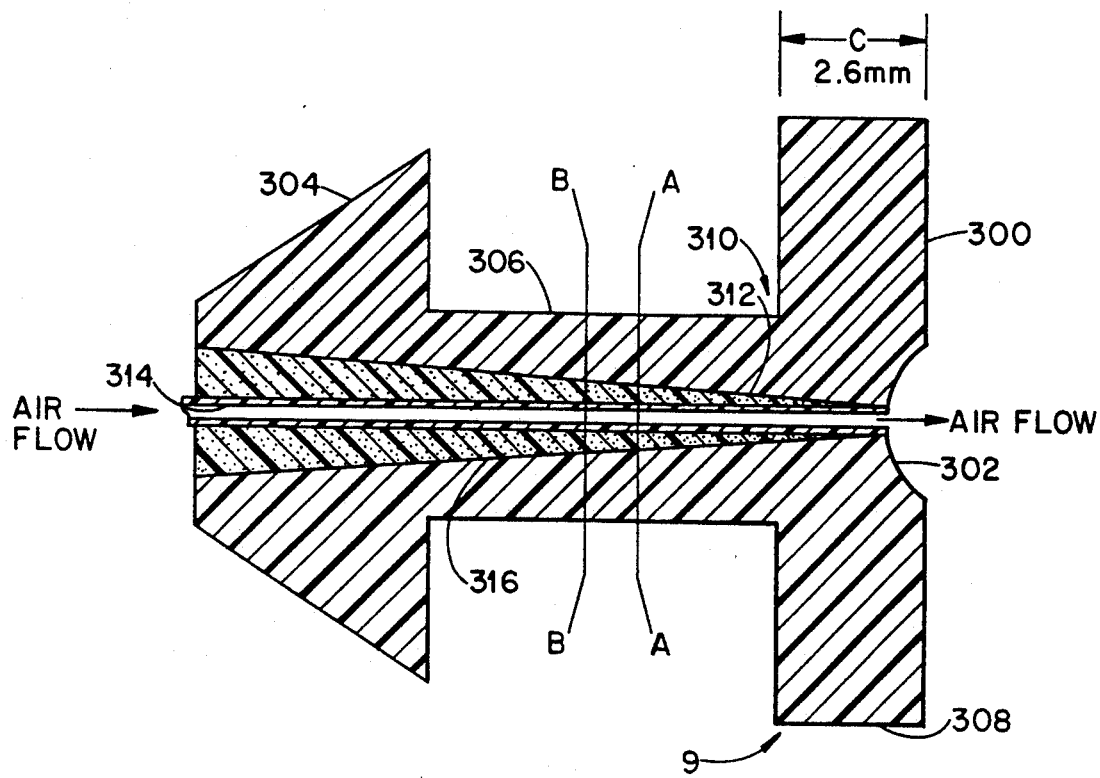
FIG. 10 is a cross-sectional view of a nozzle of the present invention.

The nozzle 9 is made to direct the air to a small area. The nozzle 9 is made so that excess air does not flow across the surface of the eye, but instead flows away from the subject. The nozzle 9, as shown in FIG. 10, comprises a wide, flat front surface 300, with a small dimpled indentation or recess 302 around the nozzle opening where the air exits from the exit end of nozzle 9. The microtubing 19 connects to the barbed fitting 304 at the air entrance end of nozzle 9. Alternatively, the flat front surface 300 of the nozzle 9 may be eliminated. However, eliminating the flat front surface 300 has two negative consequences. First, the device would induce more subject apprehension in placement. Second, there would be a greater risk of puncturing the eye with the nozzle without the flat front surface 300.

The extent of the recess 302 on the 2-dimensional face of the nozzle of the present invention is bounded by an approximately 3 mm diameter circle. The recess is relatively wide and very shallow. The extent or boundary diameter of the recess from nozzle to nozzle out 2 to 3 mm, with an approximate depth of 0.25 mm. Furthermore, the nozzle hole which emits air may be centered, or may be slightly displaced from the center of the recess in the end face of the nozzle 9 by approximately 0.005 inches in any direction.

Figure 4:
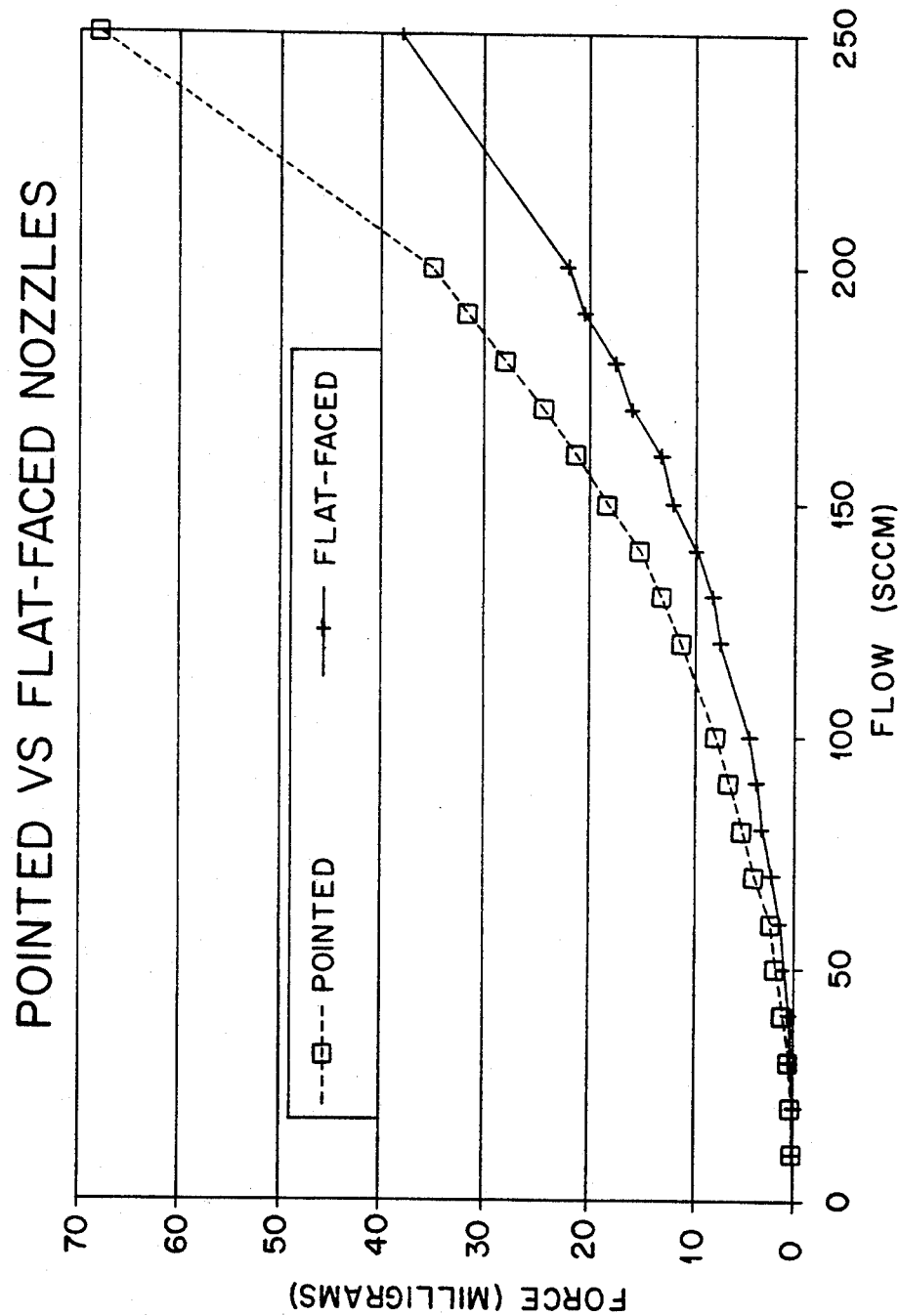
FIG. 4 is a chart showing that a flat-faced nozzle delivers less force than unsafe pointed nozzles.
Figure 5:
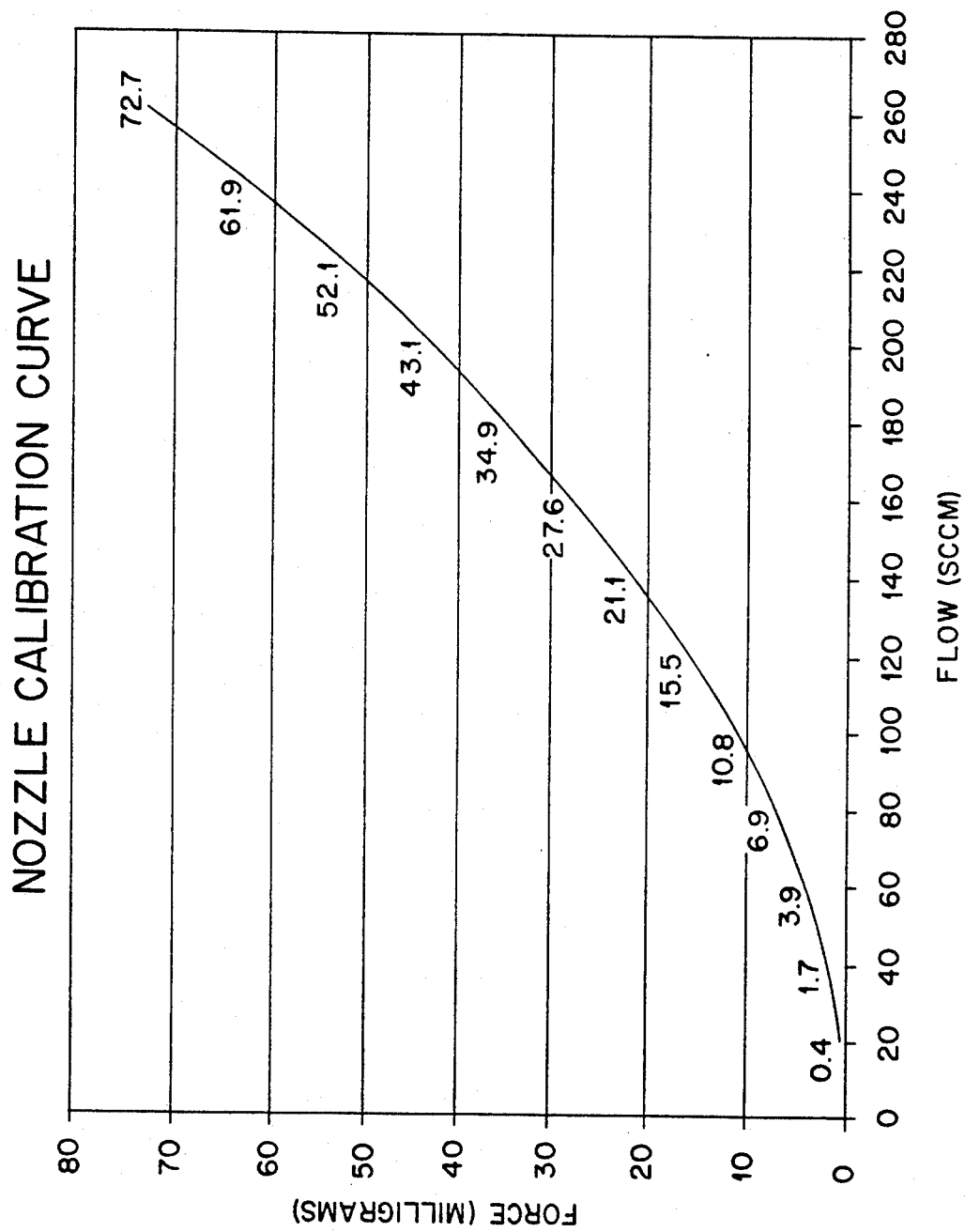
FIG. 5 is a nozzle calibration curve showing that a dimpled flat-faced nozzle delivers the same force as a pointed nozzle.

In order to achieve the strong relationship of force to flow rate that occurs with a pointed nozzle but not with an ordinary flat-faced nozzle, and without endangering the eye as a pointed nozzle would, a dimple or recess is placed on the flat face of the flat-faced nozzle 9 in the vicinity of the nozzle opening. Typically, a flat-faced nozzle attains less force at 300 SCCM than a pointed nozzle. See, for example, FIGS. 4 and 5, which show graphs of test results for various nozzle configurations. FIG. 4 shows results for a pointed nozzle front face versus a flat-faced nozzle, while FIG. 5 shows results for a flat front surface with a dimple or recess 302 (FIG. 10 configuration). Note that FIG. 5 shows a calibration curve similar to that of the pointed nozzle and different from the flat-faced nozzle (without dimple or recess 302) in FIG. 4.

Figure 10A:
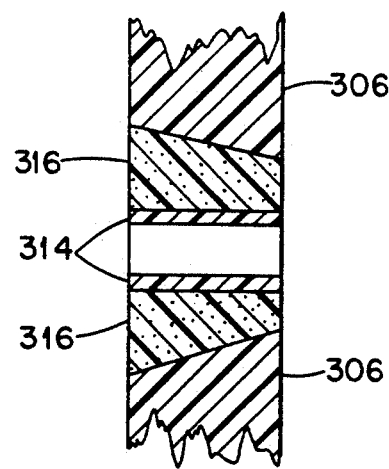
FIG. 10A is an enlarged partial view of the nozzle of FIG. 10.

According to a preferred embodiment of the invention, the nozzle shown in FIG. 10 comprises a nozzle body 310 molded of plastic material such as nylon, the nozzle body 310 having a central reduced portion 306, a barbed entrance end portion 304 for receiving a tubing 19 thereon, and an enlarged portion 308 at the air exit end, having a substantially flat front face 300 and a dimple or recess 302 in the central portion thereof where the air flow exits the nozzle. The nozzle body 310 has a tapered central elongated opening therein which receives a microtubing 314 which is secured in place within the nozzle body 310 by means of an epoxy adhesive 316. The microtubing 314 is preferably as follows:

Manufacturer: Tygon
Model No.: AAQ04091S54HL
Wall Thickness: 0.01 inches
Inner Diameter (i.D.): 0.01 inches
Material: Polyethylene FIG. 10A shows an enlarged sectional view of a portion between the lines A-B in FIG. 10, so as to more clearly show the tubing 314.

An advantage of the arrangement of FIG. 10 is that applied air pressure to the entrance end of the nozzle acts to press the tubing 314 into the tapered surface of the nozzle, thereby increasing adherence of the members together, and improving structural integrity of the nozzle construction. Also, due to the tapered internal surface 312, there is no possibility at all of the internal tubing 314 exiting from the exit end of the nozzle under the influence of the air pressure, since the exit end of the nozzle is designed with an opening too small to permit the tubing and epoxy to freely exit therefrom. Thus, patient safety is enhanced by this construction. Since a premanufactured microtubing 314 is used to define the internal passageway of the nozzle 9, there is no need for accurate molding of the plastic portion 310 thereof, and even without such accurate molding tolerances, it is still possible to produce a highly accurate and highly repeatable nozzle configuration by using the pre-manufactured microtubing 314 (having a precise internal diameter of 0.01 inches and a wall thickness of 0.01 inches to define the internal passageway of the nozzle 9).

Figure 7:
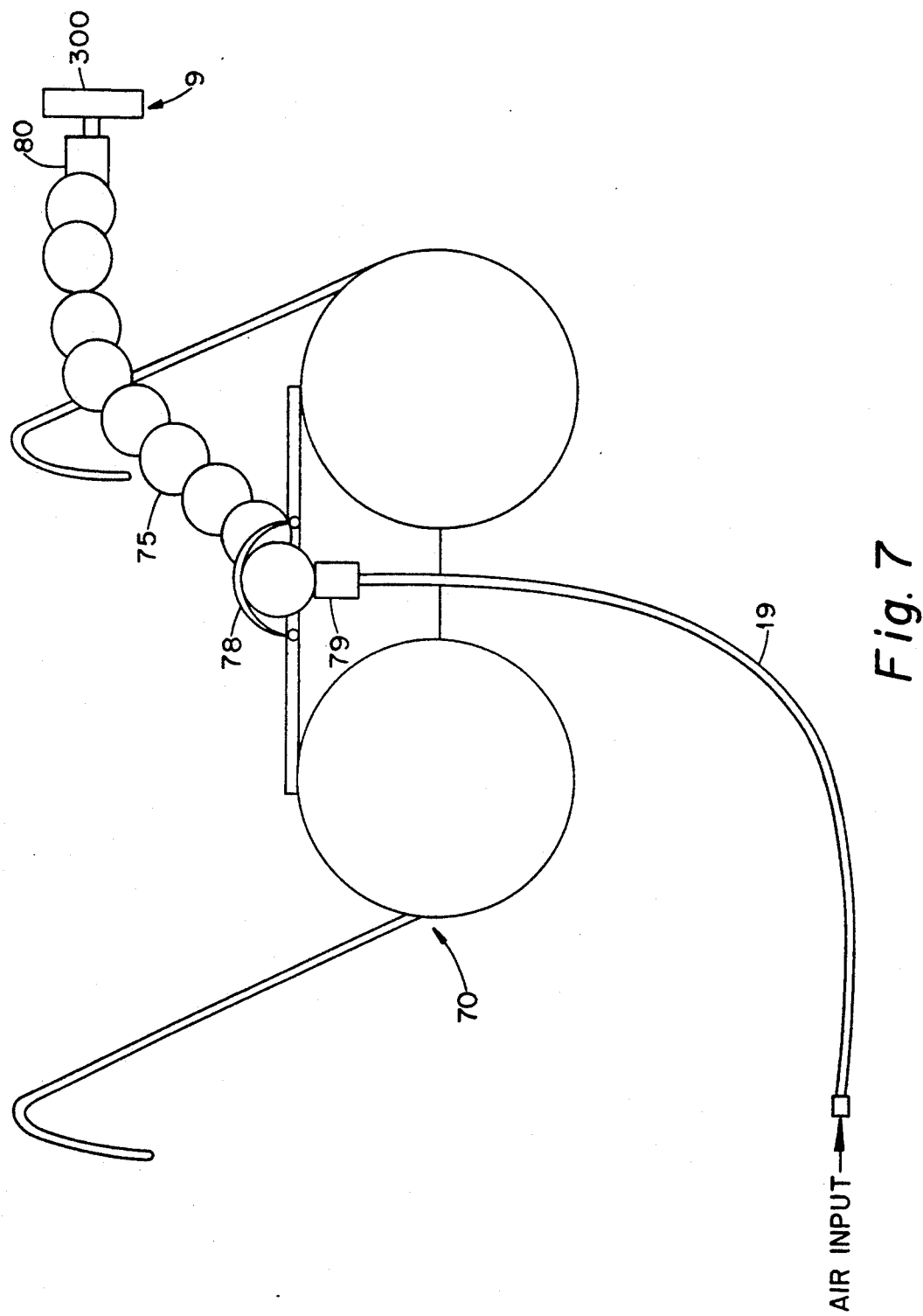
FIG. 7 shows the eye-glass frame and nozzle with the option of using the flexible positioning spheres as part of the air circuit for feeding air through friction-fit hollow, flexible, spherical units.

The nozzle 9 is located near the eye of a person to be tested and is held in place by one of three methods. By method one, the nozzle 9 is attached to a slit-lamp positioning device (MARCO-IIB slit lamp and attachment method), as shown in FIG. 6. Such devices are used by ophthalmologists and optometrists to place appliances near or in the eye. By method two, a special positioning eye-glass frame 70 is employed, as schematically shown in FIG. 7 or FIG. 9. The eye-glass frame 70 (without glass) holds the nozzle positioning apparatus to the head of the person being tested. The positioning apparatus on the eye-glass frame to used to place the nozzle 9 within about 4 to 8 mm of the corneal site to be tested. More details of the eyeglass frame positioning technique are described below with reference to FIGS. 7 and 9. By method three, a helmet assembly (FIG. 8) may be used to hold the positioning assembly for positioning the nozzle 9 relative to the eye of a patient.

Operation of the present invention will now be described in connection with a preferred form of eyeglass frame placement device. In use, as shown in FIG. 9, a tester adjusts the position of the nozzle 9 in front of the corneal location to be tested. The nozzle 9 having the dimple or recess 302 in the flat front face 300 thereof, is positioned so that the flat surface 300 thereof is from about 4 to 8 mm in front of the corneal target area. The width of the front portion of the nozzle face is about 2.6 mm (FIG. 10, dimension C), providing a measuring instrument or gauge to judge distances from about 4 mm (about 1.5 widths) through about 8 mm (about 3 widths).

As shown in FIG. 7, a first embodiment of an eyeglass-type mounting arrangement for the nozzle 9 comprises an eyeglass frame 70 having a plurality of air-tight friction-fit hollow ball members connected to the front bridge portion thereof, for example by means of a clamp 78 or an adhesive. The tube 19 leads out of the housing 11, as shown in FIG. 1. The tube 19 is connected by fitting 79 to the elongated flexible structure comprising a plurality of air-tight friction-fit hollow ball members 75 which are adjustably connected together, and which have an air passageway therethrough which leads to a nozzle 9 connected to the end hollow ball by mean of fitting 80 thereof. The elongated flexible structure comprising the hollow balls 75, which is adjustably bent and which maintains its shaped condition after being adjustably bent due to mutual friction of the hollow balls 75, is available as the "Snap-lok" system from Cedarberg Industries, Inc., Model No. 8425.

In use, the eyeglass frame 70 of FIG. 7 is placed on a head of a patient, and the adjustable friction-fit hollow ball member 75 is bent, twisted, shaped, etc. so as to direct the front face 300 of the nozzle 9 toward the eye of a patient and spaced very close to the eye of a patient. Then, operation proceeds as described in detail hereinbelow.

Alternatively, the eyeglass mounting configuration can take the form shown in FIG. 9. As shown in FIG. 9, the eyeglass frame 28 (with lenses removed, as in FIG. 7) is mounted on the head of a patient. A head strap 30 may be provided, as desired, to maintain the glasses in fixed positional relationship on the head. Attached to upper portion of the eyeglass frame is a flexible member 27 which comprises a plurality of spherical members or balls 25 within an outer tubular covering 29, made of, for example, Lycra, and which is flexible by bending (as seen in FIG. 9) and which maintains its adjusted position due to friction between the spherical members 25 in the flex-tubing device 27. This type of flex-tubing device is known in the art and is available from Cedarberg Industries, Inc (Snap-lok system).

Further provided is a Y-fitting 26 which receives a nozzle 9, 9a at the leading end thereof, and which receives the tubular air flow tube 19 (which extends from housing 110 as seen in FIG. 1). The air tube 19 is in air communication with the nozzle 9, but is out of air communication with the flex tubing 27, as seen in FIG. 9. Preferably, the Y-fitting is made of molded plastic material, such as nylon, polyethylene, etc. An advantage of the arrangement of FIG. 9 is that the air tube 19 and nozzle 9 can be easily manipulated. The flex tubing 27 serves only as an adjustment and positioning maintaining device. Operation of the arrangement of FIG. 9 is as described hereinbelow.

Figure 8:
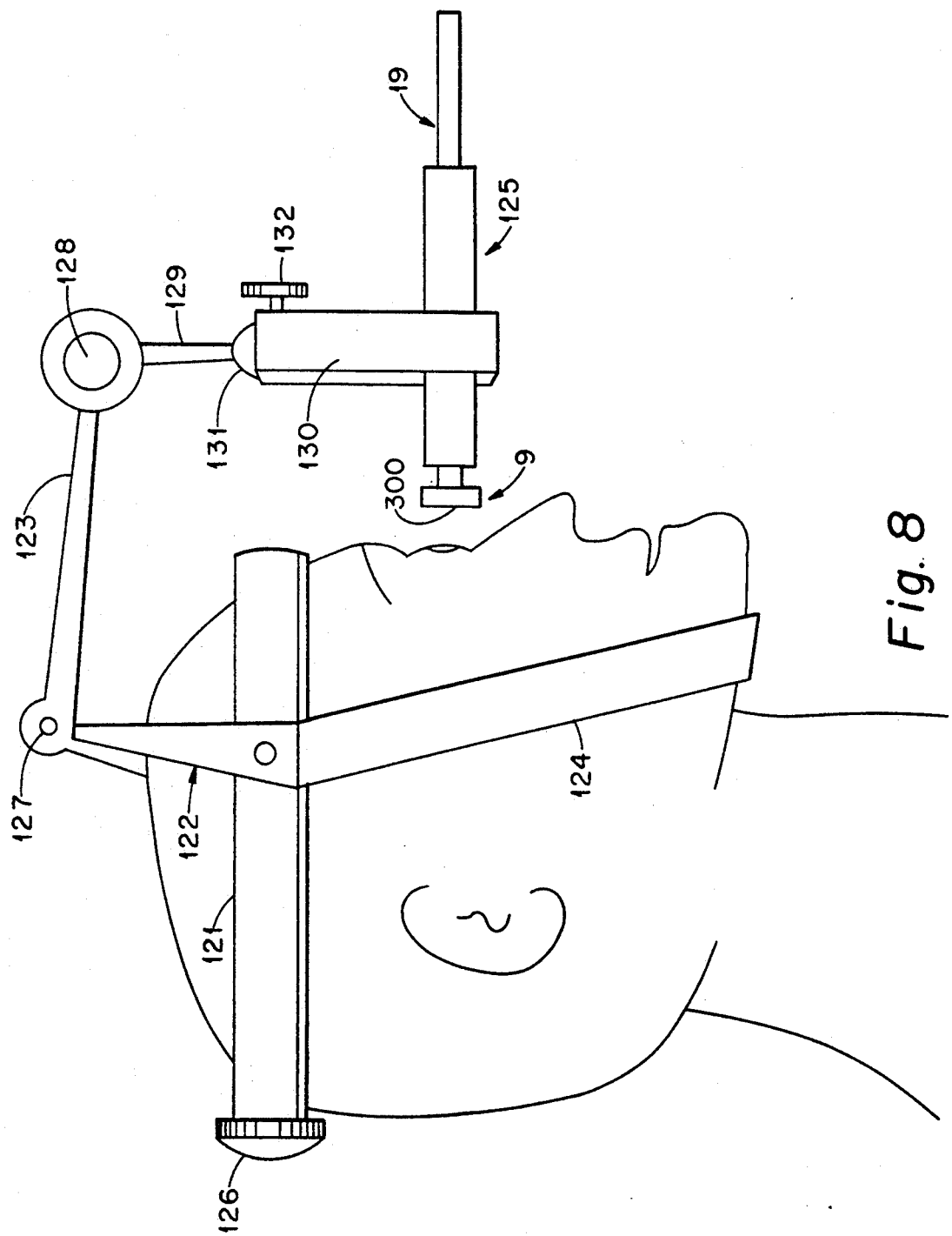
FIG. 8 shows a helmet having a nozzle, with an air tube feeding air to the nozzle.
Figure 9:
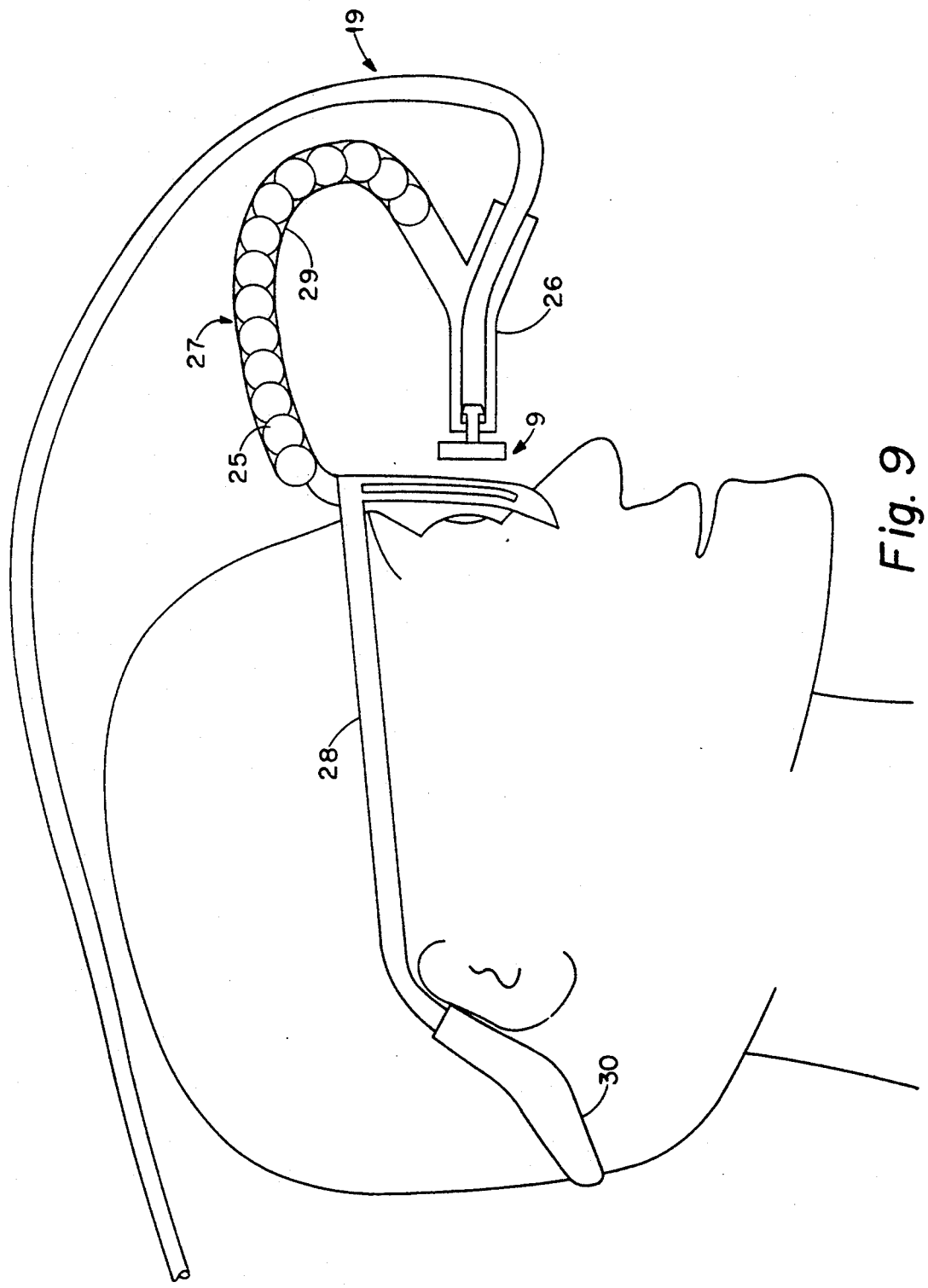
FIG. 9 is a side view of a subject's face wearing an eyeglass-frame for positioning the nozzle near the eye.

FIG. 8 shows another embodiment of the invention which comprises a head gear member 121 which is placed on the head of a patient, with a chin strap 124. An adjustment 126 is provided to adjust the size of head gear member 121 to fit the patient. An upper support member 122 is connected to the head gear member 121. An adjustment arm 123 is pivotally connected to the upper portion of support member 122, so as to be adjustable about the pivot joint 127. Sufficient friction is provided in the joint 127 to maintain arm 123 in position after it is adjusted. A multi-joint lock 128 (such as a universal adjustment joint) is provided at the free end of the arm 123, and a second adjustment arm 129 is connected thereto. The multi-joint lock is preferably a jointed arm made by McMaster-Carr, part number 85195A1. The relative orientations of the arms 123, 129 are adjusted by means of the multi-joint lock 128. The free end of arm 129 is connected to the support member 130 by means of a universal ball joint member 131 which is locked by means of a screw-type locking device 132 (which is conventional). A friction-fit slide 125 is mounted in the mounting block 130 and is preferably in fixed position within the mounting block 130. An air tube 19 (such as shown in FIG. 1) connects to the friction-fit slide member 125 and then to the nozzle 9 for supplying air to the nozzle 9. In use, the operator adjusts the position of the front face 300 of the nozzle 9 to be close to the eye of the patient, by adjusting the arms 123, 129 and joints 127, 128, 131, to place the nozzle in the desired position. After placement, the positioning is maintained in use.

It should be clear that the various air supply mechanisms for the nozzle 9, shown in FIGS. 6, 7, 8 and 9, can be used in any combination. For example, if the headrest technique of FIG. 6 is used, the hollow ball member arrangement (balls 75 and fittings 79, 80) can be clamped to the headrest portion 50 of FIG. 6 by using a clamp such as clamp 78. Then, the control member 53, 54 and 55 of FIG. 6 can be eliminated in favor of the friction fit hollow ball structure shown in FIG. 7, which is connected to the air tube 19. Similarly, the hollow ball structure 75 of FIG. 7 can be clamped to the headgear member 121 of FIG. 8 in place of the multi-joint lock arrangement of FIG. 8. In the same manner, the elongated flexible member 27 of FIG. 9 (along with its Y-fitting 26 and nozzle 9) can be clamped to the headgear member 121 of FIG. 8 in place of the multi-joint lock arrangement shown in FIG. 8, or it can be clamped to the headrest member 50 of FIG. 6, whereby the adjustment members 53, 54 and 55 of FIG. 6 can be eliminated. Such modifications and interchanging of parts among the headrest or head support members should be readily apparent, in view of the present disclosure.

The apparatus of the present invention is turned on by a power switch 11 located on its front panel (FIGS. 1 and 2). This action turns on the compressor 4 (FIG. 2). The rotometer 5 may be set at any level from 0 though about 300 SCCM (cubic centimeters per minute at standard conditions for gasses). Thresholds may be specified in units of flow rate (SCCM) or units of force (mg) by reference to a flow-to-force conversion chart (See FIG. 5). The square root of the flow rate is linear in force. When the level is set near 0 SCCM, then excess air escapes from the loose fitting connections 18 mentioned above.

The present invention allows the same external auditory stimuli to be presented to the subject, which is important, otherwise the subject might employ auditory cues to solve the problem of stimulation (i.e., was or was there not air presented). Thus, the subject has no external cues to the fact that no air force is being presented.

The loose fittings 18 allow the pump of air compressor 4 to operate continuously and the fittings to remain intact. The tester turns the calibrate switch 13 ON (FIG. 1) and verifies that adequate air flow level is achievable by means of the rotometer 5. During calibration, air is fed to the stimulate nozzle 9 (FIG. 2) which is the same as nozzle 91, but is located outside the housing 110. Air is normally fed to the calibrate nozzle 91 via port 2 of the 4-way valve 7. This action maintains a constant air resistance pathway during stimulation so that the rotometer can be set via the external dial 15 prior to stimulation. When the timer activate switch 12 or the calibrate switch 13 is activated, air flows to the stimulate nozzle 9. The purpose of the calibration switch 13 is to ensure that the air flow as adjusted by rotometer 5 is the same for stimulate nozzle 9 and calibrate nozzle 91. Calibration is accomplished by activating the calibration switch and verifying that the flow level as read on rotometer 5 has not changed from the level shown when the calibration switch is OFF. A level of 200 SCCM is typically used. The tester then turns OFF the calibrate switch 13. The calibration switch 13, when in its OFF position, directs the air flow through the "non-stimulate" path.

The tester has the subject sit in front of the slit lamp head support gear FIGS. 1 or 6), or, alternatively, the subject puts on a special positioning eye-glass frame or headgear (FIGS. 7, or 8, or 9). The tester adjusts the nozzle 9 to be about 4 to 8 mm from the corneal site to be tested in a perpendicular direction to the eye.

The tester directs the subject to respond "yes" or point upwards when the subject feels something at the test site in response to the tester's verbal prompt, "now." Similarly, the tester directs the subject to respond "no" or point downwards when nothing is felt in response to the tester's verbal prompt, "now."

The tester adjusts the rotometer by means of external dial 15 to the appropriate level. Suggested levels in the stimulation paths are from 280 through 20 SCCM. Zero level stimulations are used to confirm that the subject can differentiate no stimulus from some stimulus. When the tester pushes the timer activate switch 12, the 4-way valve 7 is activated for 0.5 seconds. Air is redirected from the "non-stimulate" air flow path to the "stimulate" air flow path (i.e., through tubing 19 and nozzle 9).

After 0.5 seconds, the 4-way valve 7 directs the air from the stimulate nozzle 9 to the calibrate nozzle 91 inside the housing (See FIG. 12). Also after 0.5 seconds, the 4-way valve 7 connects the air in the nozzle 9 to the exhaust in the housing (FIG. 12, port 3), which lowers the nozzle air pressure quickly and turns off the stimulation, thereby achieving a more rectangular stimulation pulse with quick turn-off, as seen in FIG. 11. The exhaust opening to the interior of the housing is substantially larger than the nozzle orifice to promote more rapid exhaust of air, to provide a sharper turn-off characteristic and an improved rectangular stimulation pulse. More rectangular pulses with sharper turn-off characteristics are more detectable by the person being tested and provide more reliable results.

When a person cannot reliably differentiate (estimate 50% level) between a trial giving no air force and a trial giving a set air force, a threshold is reached at that set air force.

ADVANTAGES OF THE PRESENT INVENTION

The advantage of the present invention is that it measures thresholds by delivering nonpainful, nondamaging stimulation to all persons, even those with new corneal transplants. The present invention achieves this advantage by providing an improved nozzle for stimulating specific parts of the cornea, without inadvertently stimulating nearby structures and without approaching the cornea with each stimulation.

Research by the present inventors and others (e.g., Millodot and Draeger) has indicated that people tolerate corneal esthesiometry better when the stimulation device does not approach their eyes.

By not approaching the cornea, apprehension is not induced in the person being tested. Apprehension tends to falsely lower thresholds possibly by yielding false-positive responses. See, for example, Millodot, M. 1973: Objective Measurement of Corneal Sensitivity, *Acta Opthalmologica*, 51, 325-334.

Unlike Millidot's Cochet-Bonnet type esthesiometers, the present invention does not approach the eye with each stimulation and does not damage the cornea, as confirmed by microscopic examination of the corneal following high-levels of stimulation. In the present invention, the nozzle remains in a fixed position after it is set by the operator. Even after testing fragile corneas of those with newly transplanted corneas, microscopic examination shows no sequelae.

Unlike the Draeger device which can be placed upon the eye —so that it does not approach the eye with each stimulation—the present invention does not cause pain in normal eyes when used in a nonapproaching manner.

Unlike the esthesiometer of Jalavisto, the present invention can be used to stimulate specific corneal sites and does not inadvertently stimulate other body structures.

Unlike the current laser techniques, the perceptual experience of being stimulated with the present invention is more like a momentary cool breeze, which corresponds more closely to perceptual experiences from stimulation of skin at threshold values to touch-pressure stimulation. The perception of the stimulation from the present invention is not nociceptive in normal subjects.

Even though it uses air, the present invention produces more rectangular stimulation than air would normally provide when delivered through tubes. (See FIG. 11). The present invention is engineered to stimulate only a small area of the cornea, and to control the reflected air from stimulating other nearby structures. The nozzle has a small hole of uniform diameter, and is indented or recessed slightly from a flat surface (i.e., the recess or indentation 302). The flair or indentation 302 also helps direct the used or spent air away from nearby body structures, and in conjunction with the flair protects the eye from damage by accidental contact during placing of the nozzle.

In summary, the present invention solves several problems that are inherent in currently used corneal esthesiometers. The present invention does not alter the thresholds as it measures them, as the Cochet-Bonnet esthesiometer does by damaging the cornea. The present invention does not cause pain and can be used even in low-threshold, normal patients, unlike Draeger's esthesiometer. And the present invention can stimulate discrete areas of the cornea, unlike Jalavisto's esthesiometer. Furthermore, the present invention is less likely to transmit disease (because it doesn't contact the eye), and protects the eye from inadvertent damage due to contact.

The scope of the present invention is not intended to be limited to the embodiments particularly shown in the drawings and described above in the specification. For example, in addition to measuring thresholds, the present invention may have use for measuring corneal irritation and recovery from corneal damaging procedures or diseases, etc. It will be obvious to those skilled in the art that various changes may be made without departing from the spirit and scope of the present invention as defined by the following claims.

Following is Table 1 showing parts identification for parts numbered 1-20 in FIG. 2 of the Drawings.

TABLE 1

| DIAGRAM NUMBER | DESCRIPTION | MANUFACTURER | PART # |
| --- | --- | --- | --- |
| 1 | GROUND FAULT INTERUPT | HUBELL | GFP6C15 |
| 2 | FUSE/HOLDER | RADIO SHACK | 270-364,1274 |
| 3 | POWER SUPPLY | INTERNATIONAL | IHB12-1.7 |
| 4 | COMPRESSOR | Budget Dyna-Pumps | 01-092-15 |
| 5 | ROTOMETER(METER) | MATHESON | J1-1A101-J010 |
| 6 | INTERVAL TIMER | SSAC | TSD2120P |
| 6A | 50 KOHM TIMING RESISTOR | RADIO SHACK | 271-219 |
| 7 | 4-WAY SOLENOID VALVE | SKINNER | MBD009D |
| 8 | FILTER | BALSTON | 9922-05-AQ |
| 9 | NOZZLE | BELOW | BELOW |
| 9A | UNION FITTING/BARBES FITTING | BALSTON | 14.001 |
| 9B | MICROTUBING | TYGON | AAQ04091S54HL |
| 10 | CABINET | PRECISION | 724-1028 |
| 11 | POWER SWITCH | RADIO SHACK | 275-690 |
| 12 | TIMER ACTIVATE SWITCH | RADIO SHACK | 279-605 |
| 13 | VALVE-ON CAL SWITCH | RADIO SHACK | 279-605 |
| 14 | VALVE-ON LED | RADIO SHACK | 276-001 |
| 15 | FLOW CONTROL VALVE | MATHESON | J1-1A101-J010 |
| 16 | FITTINGS | HOKE | 3RU2-316 |
| 17 | FITTINGS | HOKE | 2CM2 |
| 18 | FITTINGS | HOKE | 2CM2 |
| 19 | TYGON TUBING | TYGON | 07614EWS50HL |
| 20 | REMOTE JACK | RADIO SHACK | 274-001 |

Following is a listing of references referred to hereinabove, the entire contents of each of which are incorporated herein by reference.

REFERENCES

Beuerman, R. W. & Tanelian, D. L. (1979). Corneal pain evoked by thermal stimulation. *Pain*, 7, 1-14.

Boberg-Ans, J. (1956). On The Corneal Sensitivity. *Acta Ophthalmolgica*. 34, 149.

Cochet, P & Bonnet, R. (1959). L'esthesie corneenne. Sa mesure dans l'obsurite *Clin. Ophtalmol.*, 6, 74-78.

Davidian, M, Zaidman, G., Bainnson, D., Weinstein, C., Weinstein, S. & Drozdenko, R. (1990) Measurement and mapping of corneal sensation in normal and diseased corneas. Presented at meetings for The Association for Research in Vision and Ophthalmology.

Draeger, J. (1984). *Corneal sensitivity*. New York: Springer-Verlag. Drozdenko, R. Zaidman, G., DeLuise, V., Weinstein, S. & Weinstein, C. (1988). A new corneal microaesthesiometer. Presented at meetings of American Association of Ophthalmology.

Goldberg. (1943) *Acta Physiologica Scandanavica.*, 5, Suppl. 16. Jalavisto, E., Orma, . & Tawast, M. (1951). Aging and the relation between stimulus intensity and duration in corneal sensitivity. Acta Physiologica Scandanavica, 23, 224-233.

Kanter, E., Shafik, F., Zaidman, G., Weinstein, C., Weinstein, S. & Drozdenko, R. (1991). Age related decrease in corneal sensation (in normal and diseased corneas. Presented at meetings of The Association for Research in Vision and Ophthalmology.

Martin, X. Y. & Safran, A. B. (1988). Corneal hypesthesia. *Survey of Ophthalmology*. 23, 28-40.

Millodot, M. (1968). Psychophysical scaling of corneal sensitivity. *Psychonomic Science*, 12, 401-402.

Millodot, M. (1969). Studies on the sensitivity of the cornea. *Precision Cosmetic Digest*, 9, 1-6.

Millodot, M. (1971). Corneal sensitivity and contact lenses. *The Optician*, 162, 23-24.

Millodot, M. (1972). Diurnal variation of corneal sensitivity. *British Journal of Ophthalmology*, 56, 844-847.

Millodot, M. (1973). Objective measurement of corneal sensitivity. *Acta Ophthalmologica*, 51, 325-334.

Millodot, M. (1974). Effect of soft lenses on corneal sensitivity. *Acta Ophthalmologica*, 52, 603-608.

Millodot, M. (1975a). Do blue eyed people have more sensitive corneas than brown eyed people? *Nature*, 255, 151-152.

Millodot, M. (1975b). Effect of hard contact lenses on corneal sensitivity and thickness. *Acta Ophthalmologica*, 576-584.

Millodot, M. (1976a). Corneal sensitivity in people with the same and with different iris color. *Investigative Ophthalmology*, 15, 861-862.

Millodot, M. (1976b). Effect of the length of wear of contact lenses on corneal sensitivity. *Acta Ophthalmologica*, 54, 721-730. Millodot, M. (1977a). The influence of pregnancy on the sensitivity of the cornea. *British J. of Ophthalmology*, 61. Millodot, M. (1977b). The influence of age on the sensitivity of the cornea. *Investigative Ophthalmology & Visceral Sci.*, 16, 240-242.

Millodot, M. (1981). Corneal sensitivity. International Ophthamology Clinics *Complications of Contact Lenses*, Summer 21. Millodot, M. & Lamont. A. (1974). Influence of menstruation on corneal sensitivity. *British J. of Ophthalmology*, 58, 752-756.

Millodot, M. & Larson, W. (1967). Effect of bending of the nylon thread of the Cochet-Bonnet corneal aesthesiometer upon recorded pressure. *The Contact Lens*, 1, 5–7.

Millodot, M & O'Leary, D. J. (1981). Corneal fragility and its relationship to sensitivity. *Acta Ophthalmologica*, 59, 820–826.

Morganroth, J. & Richman, L. (1969). Changes in the corneal reflex in patients wearing contact lenses. *Journal of Pediatric Ophthalmology*, 6, 207.

Weinstein, S., Weinstein, C. & Drozdenko, R. (1987). SBIR-I, 1 R43-EYO5368-01A3, National Eye Institute--NIH, Development of a new corneal microaesthesiometer and norms.

Weinstein, S., Weinstein, C. & Drozdenko, R. (1991). SBIR-II, 2 R44-EYO5368-02A4, National Eye Institute--NIH, Development of a corneal aesthesiometer and norms II.

Weinstein, S., Weinstein, C. & Drozdenko, R. (1988). Connecticut SBIR, Development of a new corneal aesthesiometer and norms.

Zaidman, G., Gould, H., Weinstein, C., Weinstein, S. & Drozdenko, R. (1989). Corneal sensitivity mapping studies in postsurgical patients. Presented at meetings of The Association for Research in Vision and Ophthalmology.

Zaidman, G., Weinstein, C., Weinstein, S. & Drozdenko, R. (1988). A new corneal microaesthesiometer. Presented at meetings of The Association for Research in Vision and Ophthalmology.

Zaidman, G., Weinstein, C., Weinstein, S. & Drozdenko, R. (1990). A new corneal microaesthesiometer. Presented at meeting of The Association for Research in Vision and Ophthalmology.

What is claimed is:

1. An apparatus for measuring tactile sensation localized on an optic cornea of a patient, comprising:
   control means including an air compressor and airflow path means defining a stimulate air flow path and an exhaust air flow path, at least one of said air flow paths leading from said air compressor;
   stimulate nozzle means including a nozzle exit opening for delivering an air flow pulse to a localized portion of the optic cornea of the patient;
   holding apparatus for holding said stimulate nozzle means and for locating said stimulate nozzle means so that said nozzle exit opening is near to the optic cornea of the patient;
   said stimulate air flow path leading from said air compressor to said stimulate nozzle means;
   said exhaust air flow path coupling said stimulate nozzle means to an air exhaust means; and
   said air-flow path means including switching means for switching between said stimulate and exhaust air flow paths to produce a substantially rectangular air flow pulse directed from said nozzle exit opening to the optic cornea of the patient.

2. The apparatus of claim 1, wherein said switching means comprises a multi-way air valve.

3. The apparatus of claim 2, wherein said multi-way air valve comprises an electrically operable 4-way air valve.

4. The apparatus of claim 2, further comprising a rotometer connected between said multi-way air valve and said air compressor.

5. The apparatus of claim 1, wherein said air-flow path means further defines a non-stimulate air-flow path leading from said air compressor to a calibrate nozzle means which is substantially the same as said stimulate nozzle means.

6. The apparatus of claim 5, wherein said switching means alternately connects said stimulate nozzle means and said calibrate nozzle means to said air compressor via said stimulate and non-stimulate air flow paths, respectively.

7. The apparatus of claim 6, wherein said stimulate and non-stimulate air flow paths have substantially the same air flow resistance.

8. The apparatus of claim 1, wherein said stimulate nozzle means has a wide, substantially flat, front surface which is arranged for placement near the optic cornea of the patient.

9. The apparatus of claim 6, wherein said front surface of said stimulate nozzle means has a dimple or recess therein in the vicinity of said nozzle exit opening of said stimulate nozzle means.

10. The apparatus according to claim 1, further comprising a filter provided in said stimulate air flow path, with air flowing through said filter to said stimulate nozzle means.

11. The apparatus of claim 1, wherein said holding apparatus comprises an eyeglass frame position adjustment means for mounting on the head of a patient.

12. The apparatus of claim 11, wherein said eyeglass frame position adjustment means includes a flexible elongated adjustment member defining an air flow path therethrough.

13. The apparatus of claim 12, wherein said flexible elongated adjustment member comprises a plurality of substantially spherical members coupled together and each of said substantially spherical members having an opening therethrough in communication with the opening of an adjacent substantially spherical member to define said air flow path through said flexible elongated adjustment member.

14. A method for measuring tactile sensation localized on an optic cornea of a patient, comprising:
   controlling air to flow from an air compressor through at least a stimulate air flow path leading from s id air compressor;
   delivering air flow from said air compressor through said stimulate air flow path to a stimulate nozzle, said stimulate nozzle having an outlet opening for delivering an air flow pulse to the optic cornea of the patient;
   switching said air flow in said stimulate nozzle from said stimulate air flow path to an exhaust air flow path which connects the air flow path in said stimulate nozzle to an air exhaust means;
   holding said stimulate nozzle near to the optic cornea of the patient to deliver an air flow pulse from said outlet opening of said stimulate nozzle to a specific localized portion of the optic cornea of the patient.

15. The method of claim 14, wherein said air flow pulse is delivered through said stimulate nozzle with a rapid turn-off via said air exhaust mean to provide a substantially rectangular air flow pulse.

16. The method of claim 15, further comprising providing a calibrate nozzle coupled to said air compressor through a non-stimulate air flow path leading from said air compressor to said calibrate nozzle, said calibrate nozzle being substantially the same as said stimulate nozzle.

17. The method of claim 16, further comprising switching said air compressor to said non-stimulate air flow path when said stimulate nozzle is switched to said exhaust air flow path.

18. The method of claim 17, comprising alternately switching said stimulate nozzle means and said calibrate nozzle means to said air compressor via said stimulate and non-stimulate air flow paths, respectively.

19. The method of claim 18, wherein said stimulate and non-stimulate air flow paths have substantially the same air flow resistance.

20. The method of claim 14, wherein said stimulate nozzle is provided with a wide, substantially flat, front surface which is arranged for placement near the optic cornea of the patient.

21. The method of claim 20, wherein said front surface of said stimulate nozzle is provided with a dimple or recess therein in the vicinity of the air outlet opening of the stimulate nozzle.

22. The method of claim 14, wherein said stimulate nozzle is brought and held near to the optic cornea of the patient, at a distance from about 4 to about 8 millimeters, without touching the optic cornea of the patient.

23. The method of claim 14, wherein said air flow is delivered through said stimulate nozzle to an area on the surface of the optic cornea of up to about 2 millimeters in width.

24. The method of claim 14 wherein said nozzle is localized and held by an eyeglass frame position adjustment means.

25. In an apparatus for measuring tactile sensation localized on an optic cornea of a patient, comprising a stimulate nozzle means having a nozzle exit opening for delivering an air flow pulse to localized portion of the optic cornea of the patient, the improvement comprising:
position adjustment means including a head engagement member adapted to be mounted on the head of the patient, a flexible elongated adjustment member coupled to said head engagement member and including an air flow path extending therethrough, means at an opposite end of said flexible elongated adjustment member for mounting said stimulate nozzle thereto, said stimulate nozzle being in communication with said air flow path extending through said flexible elongated adjustment member, said flexible elongated adjustment member being flexibly adjustable relative to said head engagement member to orient said stimulate nozzle adjacent the optic cornea of the patient, and retaining its adjustment position after adjustment thereof.

26. The apparatus of claim 25, wherein- said flexible elongated adjustment member comprises a plurality of substantially spherical members coupled together, each of said substantially spherical members having an opening therethrough which is in communication with the opening of an adjacent substantially spherical member to collectively define said air flow path through said flexible elongated adjustment member.

27. The apparatus of claim 26, wherein said substantially spherical members are coupled together/such that frictional contact between adjacent substantially spherical members retain said adjustment position.

28. The apparatus of claim 25, wherein said head engagement member comprises a headrest against, which the head of the patient is contacted to maintain the head of the patient in a fixed position relative to said headrest.

29. The apparatus of claim 25, wherein said head engagement member comprises a headgear member engageable around the head of the patient to fixedly engage the position adjustment means to the head of the patient.

30. The apparatus of claim 25, wherein said head engagement member comprises an eyeglass frame adapted to be mounted on the head of the patient.

* * * * *